United States Patent
Darfeuille-Michaud et al.

(10) Patent No.: US 8,974,789 B2
(45) Date of Patent: Mar. 10, 2015

(54) ANTAGONISTS FOR THE PREVENTION OR TREATMENT OF INFLAMMATORY BOWEL DISEASE, AND MORE PARTICULARLY OF CROHN'S DISEASE

(75) Inventors: Arlette Darfeuille-Michaud, La Roche Blanche (FR); Paul Hofman, Nice (FR); Nathalie Rolhion, Clermont Ferrand (FR)

(73) Assignee: Universite d'Auvergne Clermont I, Clermond Ferrand (FR)

( * ) Notice: Subject to any disclaimer, the term of this patent is extended or adjusted under 35 U.S.C. 154(b) by 0 days.

(21) Appl. No.: 13/641,139

(22) PCT Filed: Apr. 15, 2011

(86) PCT No.: PCT/EP2011/055988
§ 371 (c)(1),
(2), (4) Date: Dec. 10, 2012

(87) PCT Pub. No.: WO2011/128429
PCT Pub. Date: Oct. 20, 2011

(65) Prior Publication Data
US 2013/0084292 A1    Apr. 4, 2013

(30) Foreign Application Priority Data

Apr. 15, 2010 (EP) .................................. 10305391

(51) Int. Cl.
| | | |
|---|---|---|
| A61K 39/395 | (2006.01) |
| A61K 39/00 | (2006.01) |
| A01N 43/04 | (2006.01) |
| A61K 38/16 | (2006.01) |
| C07K 16/18 | (2006.01) |
| C07K 16/28 | (2006.01) |
| C12N 15/113 | (2010.01) |
| G01N 33/68 | (2006.01) |
| A61K 38/17 | (2006.01) |
| A61K 39/40 | (2006.01) |

(52) U.S. Cl.
CPC .............. *A61K 38/164* (2013.01); *C07K 16/18* (2013.01); *C07K 16/28* (2013.01); *C12N 15/1138* (2013.01); *G01N 33/6893* (2013.01); *A61K 38/17* (2013.01); *A61K 38/177* (2013.01); *A61K 39/3955* (2013.01); *A61K 39/40* (2013.01); *A61K 2039/505* (2013.01); *C07K 2317/76* (2013.01); *C12N 2310/14* (2013.01); *G01N 2800/065* (2013.01)
USPC ........................ 424/139.1; 424/152.1; 514/23

(58) Field of Classification Search
None
See application file for complete search history.

(56) References Cited

U.S. PATENT DOCUMENTS

| | | | |
|---|---|---|---|
| 7,807,139 B2* | 10/2010 | Yang et al. ..................... 424/9.2 |
| 2010/0015600 A1 | 1/2010 | Barnich et al. |
| 2011/0189188 A1 | 8/2011 | Kliger et al. |

OTHER PUBLICATIONS

Webster's II New Riverside University Dictionary (The Riverside Publishing Company, p. 933, 1984.*
International Search Report for PCT/EP2011/055988 dated Jul. 15, 2011.
Rolhion Nathalie et al: "Adherent-invasive *Escherichia coli* in inflammatory bowel disease.", Inflammatory Bowel Diseases Oct. 2007 LNKD PubMed: 17476674, vol. 13, No. 10, (Oct. 2007), pp. 1277-1283.
Sasaki Maiko et al: "Invasive *Escherichia coli* are a feature of Crohn's disease", Laboratory Investigation, Nature Publishing Group, US, vol. 87, No. 10, (Oct. 1, 2007), pp. 1042-1054.
Nathalie Rolhion et al: "Abnormally expressed ER stress response chaperone Gp96 in CD favours adherent-invasive *Escherichia coli* invasion", Internet Citation, (Jun. 29, 2010), XP007914339, Retrieved from the Internet: URL:http://gut.bmj.com/content/early/2010/06/28/gut.2010.207456.full.pdf [retrieved on Aug. 9, 2010].
Ravi Maruvada et al: "*Escherichia coli* interaction with human brain microvascular endothelial cells induces signal transducer and activator of transcription 3 association with the C-terminal domain of Ec-gp96, the outer membrane protein A receptor for invasion", Cellular Microbiology, Blackwell Science, Oxford, GB LNKD DOI:10.1111/J.1462-5822.2008.01214.X, vol. 10, No. 11, (Nov. 1, 2008), pp. 2326-2338.
Rolhion Nathalie et al: "Strong decrease in invasive ability and outer membrane vesicle release in Crohn's disease-associated adherent-invasive *Escherichia coli* strain LF82 with the yfgL gene deleted", Journal of Bacteriology, vol. 187, No. 7, (Apr. 2005), pp. 2286-2296.

(Continued)

*Primary Examiner* — S. Devi
(74) *Attorney, Agent, or Firm* — B. Aaron Schulman, Esq.; Stites & Harbison, PLLC

(57) ABSTRACT

An antagonist of the interaction between the Gp96 receptor and *E. coli* AIEC strains, for the prevention or treatment of inflammatory bowel disease. The antagonist is for specifically blocking or reducing the interaction between Gp96 receptor and the outer membrane vesicles (OMVs), typically the outer protein membrane OmpA of *E. coli* AIEC strains. The inventions provides for pharmaceutical compositions containing such an antagonist, which may be an antibody against gp96 or OmpA, or a gp96 or OmpA polypeptide. It may be combined to an antagonist of the interaction between the CEACAM6 receptor and *E. coli* AIEC strains, such as an anti-CEACAM6 antibody, a CEACAM6 polypeptide, or a mannoside or particle having a mannose unit. The invention also relates to a method for the diagnosis of inflammatory bowel disease, or of the determination of a predisposition of a person to develop inflammatory bowel disease.

4 Claims, 3 Drawing Sheets

(56) References Cited

OTHER PUBLICATIONS

Figure 1:
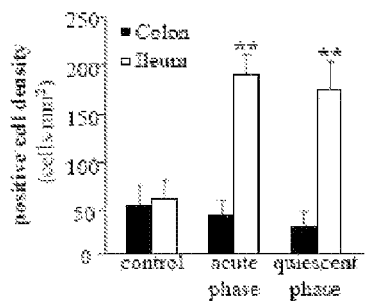

Prasadarao Nemani V et al: "Cloning and expression of the *Escherichia coli* K1 outer membrane protein A receptor, a gp96 homologue", Infection and Immunity, American Society for Microbiology, Washington, US, vol. 71, No. 4, (Apr. 1, 2003), pp. 1680-1688.

Darfeuille-Michaud et al: "High prevalence of adherent-invasive *Escherichia coli* associated with ileal mucosa in Crohn's disease", Gastroenterology, Elsevier, Philadelphia, PA LNKD-DOI:10.1053/J.Gastro.2004.04.061, vol. 127, No. 2, (Aug. 1, 2004), pp. 412-421.

Darfeuille-Michaud Arlette et al: "Presence of adherent *Escherichia coli* strains in ileal mucosa of patients with Crohn's disease", Gastroenterology, Elsevier, Philadelphia, PA, vol. 115, No. 6, (Jan. 12, 1998), pp. 1405-1413.

Sartor R Balfour et al: "Microbial host interactions in IBD: implications for pathogenesis and therapy", Current Gastroenterology Reports, Current Science, US, vol. 9, No. 6,(Dec. 1, 2007), pp. 497-507.

* cited by examiner

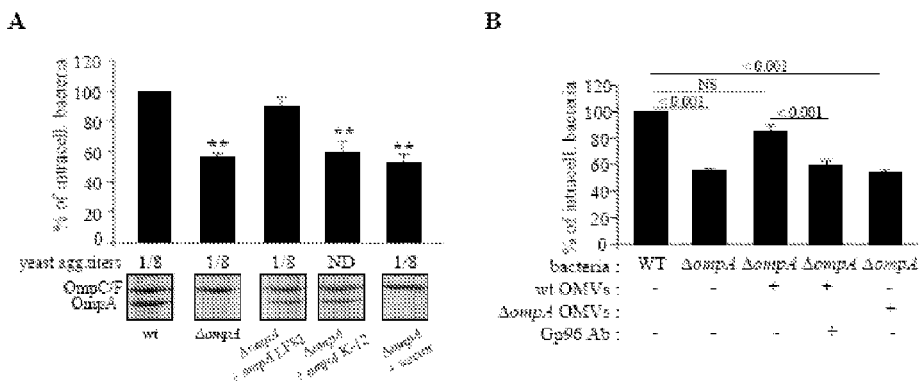

Figure 4

| | |
|---|---|
| *E. coli* K-12 | MKKTAIAIAVALAGFATVAQAAPKDNTWYTGAKLGWSQYHDTGFINNNGPTHENQ |
| AIEC LF82 | MKKTAIAIAVALAGFATVAQAAPKDNTWYTGAKLGWSQYHDTGFINNNGPTHENQ |
| | |
| *E. coli* K-12 | LGAGAFGGYQVNPYVGFEMGYDWLGRMPYKGSVENGAYKAQGVQLTAKLGYPIT |
| AIEC LF82 | LGAGAFGGYQVNPYVGFEMGYDWLGRMPYKGSVENGAYKAQGVQLTAKLGYPIT |
| | |
| *E. coli* K-12 | DDLD IYTRLGGMVWRADTKSNVYGKNHDTGVSPVFAGGVEYAITPEIATRLEYQW |
| AIEC LF82 | DDLDVYTRLGGMVWRADTKSNFDGKNHDTGVSPVFAGGVEYAITPEIATRLEYQW |
| | |
| *E. coli* K-12 | TNNIGDAHTIGTRPDNGMLSLGVSYRFGQGEAAPVVAPAPAPAPEVQTKHFTLKSDV |
| AIEC LF82 | TNNIGDAHTIGTRPDNGMLSLGVSYRFGQGEAAPVVAPAPAPAPEVQTKHFTLKSDV |
| | |
| *E. coli* K-12 | LFNFNKATLKPEGQAALDQLYSQLSNLDPKDGSVVVLGYTDRIGSDAYNQGLSERRA |
| AIEC LF82 | LFTFNKATLKPEGQAALDQLYSQLSNLDPKDGSVVVLGYTDRIGSDAYNQALSERRA |
| | |
| *E. coli* K-12 | QSVVDYLISKGIPADKISARGMGESNPVTGNTCDNVKQRAALIDCLAPDRRVEIEVKG |
| AIEC LF82 | QSVVDYLISKGIPADKISARGMGESNPVTGNTCDNVKQRAALIDCLAPDRRVEIEVKG |
| | |
| *E. coli* K-12 | IKDVVTQPQA |
| AIEC LF82 | IKDVVTQPQA |

Figure 5

SEQUENCE LISTING

<160> NUMBER OF SEQ ID NOS: 16

<210> SEQ ID NO 1
<211> LENGTH: 803
<212> TYPE: PRT
<213> ORGANISM: Homo sapiens

<400> SEQUENCE: 1

-continued

```
Met Arg Ala Leu Trp Val Leu Gly Leu Cys Val Leu Leu Thr Phe
 1               5                  10                  15

Gly Ser Val Arg Ala Asp Asp Glu Val Asp Val Asp Gly Thr Val Glu
                20                  25                  30

Glu Asp Leu Gly Lys Ser Arg Glu Gly Ser Arg Thr Asp Asp Glu Val
            35                  40                  45

Val Gln Arg Glu Glu Glu Ala Ile Gln Leu Asp Gly Leu Asn Ala Ser
 50                  55                  60

Gln Ile Arg Glu Leu Arg Glu Lys Ser Glu Lys Phe Ala Phe Gln Ala
 65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
                100                 105                 110

Asp Lys Ile Arg Leu Ile Ser Leu Thr Asp Glu Asn Ala Leu Ser Gly
                115                 120                 125

Asn Glu Glu Leu Thr Val Lys Ile Lys Cys Asp Lys Glu Lys Asn Leu
130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
                180                 185                 190

Gly Gln Phe Gly Val Gly Phe Tyr Ser Ala Phe Leu Val Ala Asp Lys
                195                 200                 205

Val Ile Val Thr Ser Lys His Asn Asn Asp Thr Gln His Ile Trp Glu
210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
                260                 265                 270

Gln Phe Ile Asn Phe Pro Ile Tyr Val Trp Ser Ser Lys Thr Glu Thr
                275                 280                 285

Val Glu Glu Pro Met Glu Glu Glu Ala Ala Lys Glu Glu Lys Glu
                290                 295                 300

Glu Ser Asp Asp Glu Ala Ala Val Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
                340                 345                 350

Asp Glu Tyr Lys Ala Phe Tyr Lys Ser Phe Ser Lys Glu Ser Asp Asp
                355                 360                 365

Pro Met Ala Tyr Ile His Phe Thr Ala Glu Gly Glu Val Thr Phe Lys
                370                 375                 380

Ser Ile Leu Phe Val Pro Thr Ser Ala Pro Arg Gly Leu Phe Asp Glu
385                 390                 395                 400

Tyr Gly Ser Lys Lys Ser Asp Tyr Ile Lys Leu Tyr Val Arg Arg Val
                405                 410                 415
```

```
Phe Ile Thr Asp Asp Phe His Asp Met Met Pro Lys Tyr Leu Asn Phe
            420                 425                 430

Val Lys Gly Val Val Asp Ser Asp Asp Leu Pro Leu Asn Val Ser Arg
        435                 440                 445

Glu Thr Leu Gln Gln His Lys Leu Leu Lys Val Ile Arg Lys Lys Leu
    450                 455                 460

Val Arg Lys Thr Leu Asp Met Ile Lys Lys Ile Ala Asp Asp Lys Tyr
465                 470                 475                 480

Asn Asp Thr Phe Trp Lys Glu Phe Gly Thr Asn Ile Lys Leu Gly Val
                485                 490                 495

Ile Glu Asp His Ser Asn Arg Thr Arg Leu Ala Lys Leu Leu Arg Phe
            500                 505                 510

Gln Ser Ser His His Pro Thr Asp Ile Thr Ser Leu Asp Gln Tyr Val
        515                 520                 525

Glu Arg Met Lys Glu Lys Gln Asp Lys Ile Tyr Phe Met Ala Gly Ser
    530                 535                 540

Ser Arg Lys Glu Ala Glu Ser Ser Pro Phe Val Glu Arg Leu Leu Lys
545                 550                 555                 560

Lys Gly Tyr Glu Val Ile Tyr Leu Thr Glu Pro Val Asp Glu Tyr Cys
                565                 570                 575

Ile Gln Ala Leu Pro Glu Phe Asp Gly Lys Arg Phe Gln Asn Val Ala
            580                 585                 590

Lys Glu Gly Val Lys Phe Asp Glu Ser Glu Lys Thr Lys Glu Ser Arg
        595                 600                 605

Glu Ala Val Glu Lys Glu Phe Glu Pro Leu Leu Asn Trp Met Lys Asp
    610                 615                 620

Lys Ala Leu Lys Asp Lys Ile Glu Lys Ala Val Val Ser Gln Arg Leu
625                 630                 635                 640

Thr Glu Ser Pro Cys Ala Leu Val Ala Ser Gln Tyr Gly Trp Ser Gly
                645                 650                 655

Asn Met Glu Arg Ile Met Lys Ala Gln Ala Tyr Gln Thr Gly Lys Asp
            660                 665                 670

Ile Ser Thr Asn Tyr Tyr Ala Ser Gln Lys Lys Thr Phe Glu Ile Asn
        675                 680                 685

Pro Arg His Pro Leu Ile Arg Asp Met Leu Arg Arg Ile Lys Glu Asp
    690                 695                 700

Glu Asp Asp Lys Thr Val Leu Asp Leu Ala Val Val Leu Phe Glu Thr
705                 710                 715                 720

Ala Thr Leu Arg Ser Gly Tyr Leu Leu Pro Asp Thr Lys Ala Tyr Gly
                725                 730                 735

Asp Arg Ile Glu Arg Met Leu Arg Leu Ser Leu Asn Ile Asp Pro Asp
            740                 745                 750

Ala Lys Val Glu Glu Glu Pro Glu Glu Glu Pro Glu Glu Thr Ala Glu
        755                 760                 765

Asp Thr Thr Glu Asp Thr Glu Gln Asp Glu Asp Glu Glu Met Asp Val
    770                 775                 780

Gly Thr Asp Glu Glu Glu Glu Thr Ala Lys Glu Ser Thr Ala Glu Lys
785                 790                 795                 800

Asp Glu Leu

<210> SEQ ID NO 2
<211> LENGTH: 358
<212> TYPE: PRT
<213> ORGANISM: Escherichia coli
```

<400> SEQUENCE: 2

```
Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
            20                  25                  30

Lys Leu Gly Trp Ser Gln Tyr His Asp Thr Gly Phe Phe Thr Ile Asn
        35                  40                  45

Asn Asn Gly Pro Thr His Glu Asn Gln Leu Gly Gly Gly Ala Phe Gly
    50                  55                  60

Gly Tyr Gln Val Asn Pro Tyr Val Gly Phe Glu Met Gly Tyr Asp Trp
65                  70                  75                  80

Leu Gly Arg Met Pro Tyr Lys Gly Ser Val Glu Asn Gly Ala Tyr Lys
                85                  90                  95

Ala Gln Gly Val Gln Leu Thr Ala Phe Thr Lys Leu Gly Tyr Pro Ile
            100                 105                 110

Thr Asp Asp Leu Asp Val Tyr Thr Arg Leu Gly Gly Met Val Trp Arg
        115                 120                 125

Ala Asp Thr Lys Ser Asn Phe Asp Gly Lys Asn His Asp Thr Gly Val
130                 135                 140

Ser Pro Val Phe Ala Gly Gly Val Glu Tyr Ala Ile Thr Pro Glu Ile
145                 150                 155                 160

Ala Thr Arg Leu Phe Thr Glu Tyr Gln Trp Thr Asn Asn Ile Gly Asp
                165                 170                 175

Ala His Thr Ile Gly Thr Arg Pro Asp Asn Gly Met Leu Ser Leu Gly
            180                 185                 190

Val Ser Tyr Arg Phe Gly Gln Gly Glu Ala Ala Pro Val Val Ala Pro
        195                 200                 205

Ala Pro Ala Pro Ala Pro Glu Val Gln Thr Lys His Phe Thr Leu Lys
    210                 215                 220

Phe Thr Ser Asp Val Leu Phe Thr Phe Asn Lys Ala Thr Leu Lys Pro
225                 230                 235                 240

Glu Gly Gln Ala Ala Leu Asp Gln Leu Tyr Ser Gln Leu Ser Asn Leu
                245                 250                 255

Asp Pro Lys Asp Gly Ser Val Val Leu Gly Tyr Thr Asp Arg Ile
            260                 265                 270

Gly Ser Asp Ala Tyr Asn Gln Ala Leu Ser Glu Arg Phe Thr Arg Ala
        275                 280                 285

Gln Ser Val Val Asp Tyr Leu Ile Ser Lys Gly Ile Pro Ala Asp Lys
    290                 295                 300

Ile Ser Ala Arg Gly Met Gly Glu Ser Asn Pro Val Thr Gly Asn Thr
305                 310                 315                 320

Cys Asp Asn Val Lys Gln Arg Ala Ala Leu Ile Asp Cys Leu Ala Pro
                325                 330                 335

Asp Arg Arg Val Glu Ile Glu Val Phe Thr Lys Gly Ile Lys Asp Val
            340                 345                 350

Val Thr Gln Pro Gln Ala
        355
```

<210> SEQ ID NO 3
<211> LENGTH: 358
<212> TYPE: PRT
<213> ORGANISM: Escherichia coli

<400> SEQUENCE: 3

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
            20                  25                  30

Lys Leu Gly Trp Ser Gln Tyr His Asp Thr Gly Phe Phe Thr Ile Asn
            35                  40                  45

Asn Asn Gly Pro Thr His Glu Asn Gln Leu Gly Ala Gly Ala Phe Gly
50                  55                  60

Gly Tyr Gln Val Asn Pro Tyr Val Gly Phe Glu Met Gly Tyr Asp Trp
65                  70                  75                  80

Leu Gly Arg Met Pro Tyr Lys Gly Ser Val Glu Asn Gly Ala Tyr Lys
                85                  90                  95

Ala Gln Gly Val Gln Leu Thr Ala Phe Thr Lys Leu Gly Tyr Pro Ile
            100                 105                 110

Thr Asp Asp Leu Asp Ile Tyr Thr Arg Leu Gly Gly Met Val Trp Arg
            115                 120                 125

Ala Asp Thr Lys Ser Asn Val Tyr Gly Lys Asn His Asp Thr Gly Val
            130                 135                 140

Ser Pro Val Phe Ala Gly Gly Val Glu Tyr Ala Ile Thr Pro Glu Ile
145                 150                 155                 160

Ala Thr Arg Leu Phe Thr Glu Tyr Gln Trp Thr Asn Asn Ile Gly Asp
                165                 170                 175

Ala His Thr Ile Gly Thr Arg Pro Asp Asn Gly Met Leu Ser Leu Gly
            180                 185                 190

Val Ser Tyr Arg Phe Gly Gln Gly Glu Ala Ala Pro Val Val Ala Pro
            195                 200                 205

Ala Pro Ala Pro Ala Pro Glu Val Gln Thr Lys His Phe Thr Leu Lys
210                 215                 220

Phe Thr Ser Asp Val Leu Phe Asn Phe Asn Lys Ala Thr Leu Lys Pro
225                 230                 235                 240

Glu Gly Gln Ala Ala Leu Asp Gln Leu Tyr Ser Gln Leu Ser Asn Leu
                245                 250                 255

Asp Pro Lys Asp Gly Ser Val Val Leu Gly Tyr Thr Asp Arg Ile
            260                 265                 270

Gly Ser Asp Ala Tyr Asn Gln Gly Leu Ser Glu Arg Phe Thr Arg Ala
            275                 280                 285

Gln Ser Val Val Asp Tyr Leu Ile Ser Lys Gly Ile Pro Ala Asp Lys
            290                 295                 300

Ile Ser Ala Arg Gly Met Gly Glu Ser Asn Pro Val Thr Gly Asn Thr
305                 310                 315                 320

Cys Asp Asn Val Lys Gln Arg Ala Ala Leu Ile Asp Cys Leu Ala Pro
                325                 330                 335

Asp Arg Arg Val Glu Ile Glu Val Phe Thr Lys Gly Ile Lys Asp Val
            340                 345                 350

Val Thr Gln Pro Gln Ala
        355

<210> SEQ ID NO 4
<211> LENGTH: 20
<212> TYPE: DNA
<213> ORGANISM: artificial sequence
<220> FEATURE:
<223> OTHER INFORMATION: oligonucleotide

<400> SEQUENCE: 4
aaagccacgt tgtgtctcaa                                               20

<210> SEQ ID NO 5
<211> LENGTH: 20
<212> TYPE: DNA
<213> ORGANISM: artificial sequence
<220> FEATURE:
<223> OTHER INFORMATION: oligonucleotide

<400> SEQUENCE: 5
ttagaaaaac tcatcgagca                                               20

<210> SEQ ID NO 6
<211> LENGTH: 67
<212> TYPE: DNA
<213> ORGANISM: artificial sequence
<220> FEATURE:
<223> OTHER INFORMATION: oligonucleotide

<400> SEQUENCE: 6
aaaggcaaaa aaaccccgc agcggggttt ttctaccaga cgagaactta gaaaaactca    60
tcgagca                                                             67

<210> SEQ ID NO 7
<211> LENGTH: 70
<212> TYPE: DNA
<213> ORGANISM: artificial sequence
<220> FEATURE:
<223> OTHER INFORMATION: oligonucleotide

<400> SEQUENCE: 7
ctcgttggag atattcatgg cgtattttgg atgataacga ggcgcaaaaa aaagccacgt   60
tgtgtctcaa                                                          70

<210> SEQ ID NO 8
<211> LENGTH: 20
<212> TYPE: DNA
<213> ORGANISM: artificial sequence
<220> FEATURE:
<223> OTHER INFORMATION: oligonucleotide

<400> SEQUENCE: 8
ggagccggag caactactgg                                               20

<210> SEQ ID NO 9
<211> LENGTH: 20
<212> TYPE: DNA
<213> ORGANISM: artificial sequence
<220> FEATURE:
<223> OTHER INFORMATION: oligonucleotide

<400> SEQUENCE: 9
acgacaccgg cgtttctccg                                               20

<210> SEQ ID NO 10
<211> LENGTH: 20
<212> TYPE: DNA
<213> ORGANISM: artificial sequence
<220> FEATURE:
<223> OTHER INFORMATION: oligonucleotide

<400> SEQUENCE: 10
gcaggcattg ctgggtaagg                                               20

```
<210> SEQ ID NO 11
<211> LENGTH: 21
<212> TYPE: DNA
<213> ORGANISM: artificial sequence
<220> FEATURE:
<223> OTHER INFORMATION: oligonucleotide

<400> SEQUENCE: 11
aatattgagc agatccccccg g                                              21

<210> SEQ ID NO 12
<211> LENGTH: 30
<212> TYPE: DNA
<213> ORGANISM: artificial sequence
<220> FEATURE:
<223> OTHER INFORMATION: oligonucleotide

<400> SEQUENCE: 12
acgcgtcgac cgttggagat attcatggcg                                      30

<210> SEQ ID NO 13
<211> LENGTH: 32
<212> TYPE: DNA
<213> ORGANISM: artificial sequence
<220> FEATURE:
<223> OTHER INFORMATION: oligonucleotide

<400> SEQUENCE: 13
cccaagcttg ggagacgaga acttaagcct gc                                   32

<210> SEQ ID NO 14
<211> LENGTH: 20
<212> TYPE: DNA
<213> ORGANISM: artificial sequence
<220> FEATURE:
<223> OTHER INFORMATION: oligonucleotide

<400> SEQUENCE: 14
gggtgtggtg gactcagatg                                                 20

<210> SEQ ID NO 15
<211> LENGTH: 20
<212> TYPE: DNA
<213> ORGANISM: artificial sequence
<220> FEATURE:
<223> OTHER INFORMATION: oligonucleotide

<400> SEQUENCE: 15
gttgccagac catccgtact                                                 20

<210> SEQ ID NO 16
<211> LENGTH: 19
<212> TYPE: RNA
<213> ORGANISM: Artificial Sequence
<220> FEATURE:
<223> OTHER INFORMATION: for synthesis of siRNA

<400> SEQUENCE: 16
ucaguuggau ggauuaaau                                                  19
```

US 8,974,789 B2

ANTAGONISTS FOR THE PREVENTION OR TREATMENT OF INFLAMMATORY BOWEL DISEASE, AND MORE PARTICULARLY OF CROHN'S DISEASE

The invention relates to peptidic or polypeptidic antagonists for the prevention or treatment of inflammatory bowel disease, and more particularly of Crohn's disease. It also relates to a method for diagnosing this disease.

Inflammatory bowel disease (IBD) mainly consists of two disorders, ulcerative colitis (UC) and Crohn's disease (CD), with a combined prevalence of about 150-200 cases per 100,000 in Western countries. The abnormal inflammatory response observed in IBD requires interplay between host genetic factors and the intestinal microbiota [1, 2]. Several lines of evidence support the notion that IBD results from an excessive immune response to gut commensal organisms [1, 3]. However, the disease could result from a problem in the composition of the microflora leading to generalized or localized dysbiosis. Increased numbers of mucosa-associated *E. coli* are observed in patients with CD [4, 5, 6, 7, 8, 9].

These mucosa-associated *E. coli*, called AIEC for Adherent-Invasive *Escherichia coli*, are able to adhere to and to invade intestinal epithelial cells (IEC) [6, 10], and to colonize the ileal mucosa of CD patients [11]. AIEC are able to promote their own colonization in genetically predisposed patients who develop ileal CD by inducing increased expression of CEACAM6 (carcinoembryonic antigen-related cell adhesion molecule 6), which acts as a receptor for these bacteria [12].

WO 2006/040481 describes the abnormal overexpression of the CEACAM6 (carcinoembryonic antigen-related cell adhesion molecule 6) receptor at the ileal level in patients suffering from Crohn's disease and a remarkable affinity between this receptor and the *E. coli* AIEC strains. It also describes an in vitro method for the diagnosis of Crohn's disease based on the evaluation of the expression on this receptor in a sample of a subject to be tested and the use of mannosides or of anti-CEACAM6 antibodies or peptides as a medicament intended for the prevention of treatment of Crohn's disease.

Among the virulence factors harboured by AIEC strains, outer membrane vesicles (OMVs), by delivering bacterial effectors to host cells, play a role in the invasive ability of AIEC reference strain LF82 [13]. Through their interaction with eukaryotic cells, OMVs, which are 50-200 nm proteoliposomes, can deliver vesicle components and virulence factors to or into host cells [14, 15]. One of the major proteins on the surface membrane of OMVs is the OmpA protein, a multifaceted protein with many diverse roles in adhesion, invasion and intracellular bacteria persistence [16, 17, 18]. Among its biological roles, it is implicated in the ability of meningitis-associated *E. coli* to invade brain microvascular endothelial cells (BMEC) via the interaction with the endothelial cell glycoprotein EcGp96 [19, 20]. An homolog of EcGp96 glycoprotein is expressed by IEC: the endoplasmic reticulum (ER) localized stress response chaperone Gp96 [21]. Interestingly, ER stress was recently reported to have a key role in both UC and CD patients after the discovery of single nucleotide polymorphisms within the XBP1 gene encoding the transcription factor XBP1, a key component of the ER stress response [22, 23].

WO 2009/113074 is related to the heat shock or stress protein Gp96 which is constitutively expressed and normally resides in the lumen of the endoplasmic reticulum. Gp96 is an intensively studied stress protein. TLRs are an important family of receptors that contribute to innate immunity and regulate adaptive immunity. Defects in TLR expression or function can lead to increased susceptibility to infection with various pathogens. In contrast, excessive or inappropriate TLR signalling is associated with pathological processes, like LPS-induced endotoxin shock in sepsis, certain autoimmune and inflammatory conditions and cancer. Thus, mechanisms that regulate TLR expression and function may be critical for shaping both immunity to pathogens and pathologic immune reactions. Recent evidence reveals that Gp96 is the unique and obligatory master chaperone for TLRs. It is essential for signalling by TLRs1-9 [30]. Based on this and on observations in the prior art that forced Gp96 or TLR4 expression may be involved in the induction of autoimmune disease, it has been postulated that inhibition of Gp96 activity may be used as a therapeutic target to lessen TLRs malfunctioning in various disease states. Among the disorders that may result from TLRs malfunctioning, WO 2009/113074 recites allergic reactions, atherosclerosis, cardiac dysfunction in sepsis, congestive heart failure, ischemic injury, acute allograft rejection, infection-associated preterm birth, cancer, systemic responses to invading pathogens during sepsis, inflammatory conditions, and so on. WO 2009/113074 reminds that past investigative strategies focused on the development of TLRs antagonists capable of inhibiting innate immune responses for the potential treatment of a vast array of immuno-regulated disorders, and on the targeting of CD91, a receptor for Gp96. WO 2009/113074 rather suggests that antagonizing Gp96 may be an effective approach for the treatment of these disease conditions. This document thus proposes a therapeutic unspecific approach aiming at mediating TLR's signalling using antagonists of Gp96. It is proposed in a completely unspecific and theoretical manner that antagonizing gp96 would have a therapeutic value for a very wide range of very different conditions, disorders and diseases: sepsis, septic shock, endotoxin shock, endotoxinaemia, systemic inflammatory response syndrome (SIRS), autoimmune diseases (IBD and CD are mentioned among a very large list of autoimmune diseases), diseases involving inflammation of the respiratory tract, auto-inflammatory disease, ischemia-reperfusion injury related disorders, cardiovascular diseases, heavy metal induced diseases, kidney diseases, infectious diseases, cancer, inflammation-induced cancer, preterm birth, surgery complications, acute allograft rejection. The Gp96 inhibitors may be Gp96-derived peptides, antibodies and fusion proteins.

There is still a need for therapeutic and diagnosis approaches that are more closely related and specific to inflammatory bowel diseases, and more particularly Crohn's disease.

SUMMARY OF THE INVENTION

Inventors work: Immunohistochemistry on tissue arrays showed that Gp96 is strongly expressed at the apical plasma membrane of the ileal epithelial cells of 50% of CD patients and not expressed in controls. Invasion experiments in the presence of antibodies raised against Gp96, or after transfection of Intestine-407 cells with Gp96 siRNA, indicated that Gp96 is essential to promote AIEC reference strain LF82 invasion allowing, via the recognition of the outer membrane protein OmpA, OMVs to fuse with intestinal epithelial cells. Gp96 is overexpressed on the apical surface of ileal epithelial cells in CD patients and acts as a host cell receptor for OMVs, promoting AIEC invasion. From the results shown here, it is deemed that AIEC bacteria could take advantage of the abnormal expression of Gp96 in CD patients to invade the ileal mucosa. These results were also published in [31] which content is entirely incorporated herein by reference.

The authors of the present invention then focussed on identifying compounds, preferably peptidic or polypeptidic compounds for the prevention or treatment of inflammatory bowel disease. At the heart of the invention is the demonstration, made by the inventors, of this abnormal overexpression of the Gp96 receptor at the ileal level in patients suffering from inflammatory bowel disease, in particular Crohn's disease, of a remarkable affinity between this receptor and the outer protein membrane OmpA of *E. coli* AEC strains and of the interest of blocking or reducing this interaction using compounds, preferably peptidic or polypeptidic compounds that may bind to Gp96 or to OmpA.

This open the way to a novel therapeutic way to prevent and/or treat these disorders, based on the inhibition of the specific interaction between the intestinal epithelial cells and *E. coli* AIEC, and on the inhibition of potential invasion of these cells by this microorganism and/or other pathogens that may be present at the same time. This new therapeutic way may be beneficial for patients having Gp96 expression on the intestinal epithelial cells, in particular at the ileal level, especially at the apical plasma membrane of the ileal epithelial cells, and more specifically to such patients wherein *E. coli* AIEC is present or other pathogenic bacteria also expressing an outer membrane protein A able to recognize Gp96.

An object of the present invention is therefore an antagonist of the interaction between the Gp96 receptor and *E. coli* AIEC strains, for the prevention or treatment of an inflammatory bowel disease, such as ulcerative colitis (UC) and Crohn's disease (CD).

An object of the invention is in particular such an antagonist for use as an inhibitor of the interaction of the Gp96 receptor and AIEC strains, in particular its outer protein membrane OmpA. More particularly, this antagonist is for use as an inhibitor of the interaction of the Gp96 receptor and *E. coli* AIEC strains, in particular its outer protein membrane OmpA, in view of the prevention or treatment of an inflammatory bowel disease, such as ulcerative colitis (UC) and Crohn's disease (CD).

An object of the invention is also such an antagonist for use to inhibit the invasion of intestinal epithelial cells by the *E. coli* AIEC strains. This is in view of the prevention or treatment of an inflammatory bowel disease, such as ulcerative colitis (UC) and Crohn's disease (CD).

The binding of OmpA to Gp96 receptor may also contribute to invasion of the intestinal epithelial cells by other pathogens. Therefore, another object of the invention is such an antagonist for use to inhibit the invasion of intestinal epithelial cells by the *E. coli* AIEC strains and/or other pathogens, such as pathogenic bacteriae present inside the gastrointestinal lumen.

Another object of the invention is the combination of such an antagonist and an antagonist of the interaction between CEACAM 6 and *E. coli* AIEC strains, in the prevention and/or treatment of an inflammatory bowel disease, such as ulcerative colitis (UC) and Crohn's disease (CD).

Another object of the present invention is an in vitro method for the diagnosis of inflammatory bowel disease, such as ulcerative colitis (UC) and Crohn's disease (CD), or of the determination of a predisposition of a person to develop inflammatory bowel disease, such as ulcerative colitis (UC) and Crohn's disease (CD), in which it is determined whether the level of expression of the Gp96 receptor in a biological sample from a subject to be tested is higher than the level of expression in a control sample, which is indicative of inflammatory bowel disease, or of a predisposition of the subject tested to develop inflammatory bowel disease.

Another object of the present invention is an in vitro method for screening candidate substances for the prevention or treatment of inflammatory bowel disease, such as ulcerative colitis (UC) and Crohn's disease (CD), comprising:
(i) bringing the Gp96 receptor, in soluble form or expressed at the surface of the cell, into contact with at least one *E. coli* AIEC strain, in the presence of a substance to be tested;
(ii) determining the capacity of the substance to specifically inhibit the interaction between the Gp96 receptor and said strain, and selecting and/or identifying said substance.

DETAILED DESCRIPTION

The first object of the present invention is an antagonist of the interaction between the Gp96 receptor and *E. coli* AIEC strains, for the prevention or treatment of inflammatory bowel disease, and more particularly for the prevention or treatment of Crohn's disease.

According to a first embodiment, the antagonist is a peptidic or polypeptidic antagonist which specifically blocks or reduces by at least 30% the interaction between Gp96 receptor and *E. coli* AIEC strains.

In an embodiment, the peptidic or polypeptidic antagonist is one which specifically blocks or reduces the interaction between Gp96 receptor and the outer membrane vesicles (OMVs) of *E. coli* AIEC strains. The OMVs are those present at the surface of the bacteria and/or free OMVs detached from the bacteria.

According to another embodiment, the peptidic or polypeptidic antagonist specifically blocks or reduces the interaction between Gp96 receptor and the outer protein membrane OmpA of *E. coli* AIEC strains. The OmpA is present at the surface of the bacteria and/or of free OMVs detached from the bacteria.

According to an embodiment, the peptidic or polypeptidic antagonist is an anti-Gp96 antibody.

According to another embodiment, the peptidic or polypeptidic antagonist is an anti-OmpA antibody.

According to another embodiment, the peptidic or polypeptidic antagonist comprises both an anti-OmpA antibody and an anti-Gp96 antibody.

"Antibody" is used in the broadest sense to designate any antibody that may bind to Gp96 or to OmpA wherein this binding makes that the binding between Gp96 and OmpA is rendered impossible. In an embodiment, the antibody is specific to the Gp96-specific binding amino acid sequence of OmpA or to the OmpA-specific binding amino acid sequence of Gp96. "Antibody" includes monoclonal antibodies, polyclonal antibodies, single-chain antibodies and antigen binding fragments of these antibodies which exhibit the desired biological activity. The monoclonal antibodies may be murine, chimeric or humanized. The term "antibody" refers to any full-length antibody or functional fragment of an antibody (obtained by genetic engineering or not), comprising, or consisting of, at least one antigenic combination site, allowing said antibody to bind to at least one antigenic determinant of an antigenic compound. By way of example of antibody fragments, there may be mentioned the fragments Fab, Fab', F(ab')$_2$ and the single-chain variable fragments (scFv chains). The antibodies used in the present invention are antibodies specific for the antigen. They are preferably monoclonal antibodies or monospecific polyclonal antibodies, that is to say that they specifically recognize only one epitope. The production of monoclonal antibodies or of monospecific polyclonal sera, or of antibodies obtained by screening genomic libraries, useful in the context of the invention are conventional techniques.

An anti-Gp96 polyclonal antibody may, inter alia, be obtained by immunizing an animal such as a rabbit, a mouse and the like with the aid of the soluble Gp96 receptor or of an antigenic fragment thereof, collecting and then depleting the antiserum obtained on, for example, an immunoadsorbent containing the receptor according to methods known per se to a person skilled in the art.

Several anti-Gp96 monoclonal or polyclonal antibodies have been developed and marketed:
- anti-Grp94 H-212, Santa Cruz Biotechnology, Santa Cruz, USA;
- Rat anti-Grp94 Monoclonal Antibody (9G10), product #SPA-850, Stressgen®, Assay Designs, Ann Arbor, Mich. 48108 USA;
- Rat anti-Grp94 Monoclonal Antibody (9G10) Dylight 488 Conjugate; product #SPA-850-488, Stressgen®, Assay Designs, Ann Arbor, Mich. 48108 USA;
- Rat anti-Grp94 Monoclonal Antibody (9G10) product #SPA-850, Stressgen®, Assay Designs, Ann Arbor, Mich. 48108 USA
- Rabbit Anti-Gp96 (N-term) Monoclonal Antibody, Clone ZMD.287, Invitrogen, Carlsbad, Calif., USA.

The native Gp96 amino acid sequence is as depicted on SEQ. ID NO:1 and may be used in whole or in part to design antibodies. Variant sequences may also be used as described below.

The amino acid sequences for LF82 and K-12 differ by 5 amino acids as depicted on FIG. 5. Either sequence may be used to design the antibodies. As an alternative, use is made of the whole LF82 amino acid sequence or a fragment that include at least one of the amino acids variations: Val115, Phe132, Asp133, Thr223, Ala269. In some specific embodiments, the amino acid sequence comprises Asp133 and Thr223, or Phe132, Asp133 and Thr223. Variant sequences may also be used as described below.

Generally, other monoclonal antibodies may be obtained according to the conventional method of lymphocyte fusion and hybridoma culture described by Kohler and Milstein, (1975). Other methods for preparing monoclonal antibodies are also known (Harlow et al., ed., 1988 "Antibodies: a laboratory manual"). The monoclonal antibodies may be prepared by immunizing a mammal (for example a mouse, a rat, a rabbit or even a human being, and the like) and using the lymphocyte fusion technique leading to hybridoma (Köhler and Milstein, 1975).

Alternative techniques to this customary technique exist. It is possible, for example, to produce monoclonal antibodies by expressing a nucleic acid cloned from a hybridoma. It is also possible to produce antibodies by the phage display technique by introducing cDNAs for antibodies into vectors, which are typically filamentous phages which exhibit gene libraries V at the surface of the phage (for example fUSE5 for *E. coli*, Scott, 1990). Protocols for constructing these antibody libraries are described in Marks et al. (1991).

In an embodiment, the antagonist is a Gp96 or OmpA polypeptide.

The native Gp96 amino acid sequence is as depicted on SEQ ID NO:1.

The native OmpA amino acid sequence for *E. coli* AIEC LF82 is as depicted on SEQ ID NO:2.

The native OmpA amino acid sequence for *E. coli* K-12 is as depicted on SEQ ID NO:3.

A "Gp96 or OmpA polypeptide" includes both native sequence Gp96 or OmpA polypeptide, Gp96 or OmpA polypeptide variants, and chimeric Gp96 or OmpA polypeptides.

"Native sequence Gp96 or OmpA polypeptide" comprises a polypeptide having the same amino acid sequence as the corresponding Gp96 or OmpA polypeptide found in the human or derived therefrom. The native sequence Gp96 or OmpA polypeptide can be natural, i.e. isolated from human, recombinant, i.e. produced by recombinant means, or synthetic, i.e. produced by synthesis.

The native sequence Gp96 or OmpA polypeptide encompasses the full-length amino acid sequence of the corresponding Gp96 or OmpA polypeptide found in the human or a naturally-occurring truncated or secreted form. It also encompasses a fragment of the full-length amino acid sequence which is capable of binding its target OmpA or Gp96.

"Gp96 or OmpA polypeptide variants" means a polypeptide which amino acid sequence differ from the corresponding native sequence Gp96 or OmpA polypeptide and which keep the function of the full-length sequence in terms of specific binding to its target. Such a full-length Gp96 or OmpA polypeptide variant or a fragment may have at least about 80, 81, 82, 83, 84, 85, 86, 87, 88, 89, 90, 91, 92, 93, 94, 95, 96, 97, 98 or 99% amino acid sequence identity with the corresponding, either full-length or partial (fragment), native sequence Gp96 or OmpA polypeptide.

"Chimeric Gp96 or OmpA polypeptides" are Gp96 or OmpA polypeptides fused to a heterologous amino acid sequence. The present invention encompasses chimeric Gp96 or OmpA polypeptides comprising a fraction of the Gp96 or OmpA polypeptide, e.g. the specific binding domain, and supplemental amino acids.

In an embodiment, the chimeric Gp96 or OmpA polypeptide is a fusion protein comprising a Gp96 or OmpA polypeptide and an immunoglobin domain. "Immunoglobin domain" means a Fc domain, a heavy chain or a light chain. In a preferred embodiment, the immunoglobin domain is a Fc sequence. It may be in particular a Fc from a human IgG1.

According to another embodiment, the peptidic or polypeptidic antagonist is a fragment of native or variant Gp96 which is able to bind with OmpA of *E. coli* AIEC strains, which binding blocks or reduce the interaction between *E. coli* AIEC strains and the Gp96 receptor at the surface of the intestinal epithelial cells.

According to another embodiment, the peptidic or polypeptidic antagonist is a fragment of native or variant OmpA of *E. coli* AIEC strains which is able to bind with Gp96, which binding blocks or reduce the interaction between *E. coli* AIEC strains and the Gp96 receptor at the surface of the intestinal epithelial cells.

"Fragment" means at least 5, preferably at least 8, more particularly at least 10, 15 or 20 continuous amino acids sequence of the native protein (Gp96 or OmpA) or of one of its variants according to the invention.

The amino acid sequences for LF82 and K-12 differ by 5 amino acids as depicted on FIG. 5. Either sequence may be used to design the polypeptidic or peptidic antagonists of the invention, including antibodies. As an alternative, use is made of the whole LF82 amino add sequence or a fragment that include at least one of the amino acids variations: Val115, Phe132, Asp133, Thr223, Ala269. In some specific embodiments, the amino acid sequence comprises Asp133 and Thr223, or Phe132, Asp133 and Thr223.

According to another embodiment, the antagonist is a siRNA which silences the qp96 gene.

A small interfering RNA or siRNA is a double stranded RNA (dsRNA) that may have from 10 to 50 nucleotides in length and which reduces expression of the target gene. Portions of the first strand are complementary to the target gene, i.e. it has sufficient complementarity to hybridize to the target gene, for example there is at least 80% identity to the target gene or to a portion thereof.

The peptidic or polypeptidic antagonists according to the invention may be incorporated in a pharmaceutical composition, preferably for oral administration.

These compositions may be administered orally for example, for example in the form of tablets, capsules or granules with immediate or controlled release.

A solid composition for oral administration is prepared by adding to the peptidic or polypeptidic antagonist a filler and, where appropriate, a binder, a disintegrating agent, a lubricant, a colorant or a flavour corrigent, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include polyvinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin.

Examples of lubricants include magnesium stearate, talc, polyethylene glycol, silica and hardened vegetable oils. The colorant may be any one of those authorized for use in medicaments.

Examples of flavour corrigents comprise powdered cocoa, mint in herb form, aromatic powder, mint in oil form, borneol and powdered cinnamon. It should be understood that the tablet or granule may be suitably coated with sugar, gelatine or the like.

In a particular embodiment, the pharmaceutical composition further comprises an antagonist of the interaction between the CEACAM6 receptor and *E. coli* AIEC strains.

This second antagonist may be any one described in WO2006/0404481 to which the person skilled in the art may refer. As disclosed on this document, this antagonist may be any peptidic or polypeptidic antagonist of this interaction.

In an embodiment, the antagonist of interaction between the CEACAM6 6 (designated as Cd66c in WO2006/0404481) receptor and *E. coli* AIEC strains is an anti-CEACAM6 antibody.

In another embodiment, the antagonist is a CEACAM6 polypeptide that may specifically interact with the AIEC strain and impede the binding to CEACAM6. Such polypeptides have been disclosed in WO2006/0404481 and WO01/013937.

The definitions of antibody and polypeptide given with respect Gp96 and OmpA apply also to the CEACAM6 antibodies and polypeptides that may be used as antagonists. These may be in particular polyclonal or monoclonal antibodies, murine, chimeric or humanized antibodies, native polypeptides or derivatives, full-length or fragments, chimeric polypeptides such as fusion polypeptides, and so on.

In another embodiment, the antagonist for the CEACAM6/AIEC strain interaction, is a mannoside, such as D-mannose, methyl-D-mannose, or a particle carrying one or more mannose units. By definition, the term mannoside therefore includes D-mannose and the compounds capable of releasing D-mannose by hydrolysis, for example polysaccharides and oligosaccharides which release D-mannose by hydrolysis (homo- or heterosaccharides), and any derivatives of D-mannose capable of interacting with the adhesin FimH of the AIEC strains. The particles carrying one or more mannose units may be for example inert beads or particles or living or dead cells.

The present invention also relates to a pharmaceutical composition comprising an antagonist of the interaction between Gp96 and OmpA and further an antagonist of interaction between the CEACAM6 receptor and *E. coli* AIEC strains and a pharmaceutically acceptable carrier.

The present invention also relates to a pharmaceutical composition comprising an antagonist of the interaction between Gp96 and OmpA and further an antagonist of interaction between the CEACAM6 receptor and *E. coli* AIEC strains, for simultaneous, separated or differed administration.

The present invention may thus relates to a pharmaceutical kit comprising a first composition containing an antagonist of the interaction between Gp96 and a pharmaceutically acceptable carrier and OmpA and a second composition containing an antagonist of interaction between the CEACAM6 receptor and *E. coli* AIEC strains and a pharmaceutically acceptable carrier.

The effective doses and dosages for administration of the peptidic or polypeptidic antagonists, intended for the prevention or treatment of inflammatory bowel disease, and particularly Crohn's disease, depend on a large number of factors, and for example on the nature of the antagonist, the size of the patient, the stage of the disease, the specific pharmaceutical composition used and the observations and conclusions of the attending physician.

For example, in the case of an oral administration, for example a tablet or a capsule, a possible suitable dosage is between about 0.1 mg/kg and about 100 mg/kg of body weight per day, and preferably between about 0.5 mg/kg and about 50 mg/kg of body weight per day, more preferably between about 1 mg/kg and about 10 mg/kg of body weight per day and preferably still between about 2 mg/kg and about 5 mg/kg of body weight per day of active material.

If representative body weights of 10 kg and 100 kg are considered in order to illustrate the daily dosage range by the oral route which may be used as described above, suitable dosages will be between about 1-10 mg and 1000-10 000 mg per day, preferably between about 5-50 mg and 500-5000 mg per day, preferably still between about 10.0-100.0 mg and 100.0-1000.0 mg per day, and more preferably between about 20.0-200.0 mg and about 50.0-500.0 mg per day, of active ingredient.

These dosage ranges represent total quantities of active ingredient per day for a given patient. The number of administrations per day at which a dose is administered may vary widely, especially according to pharmacokinetic factors.

The invention therefore also relates to the use of an antagonist, preferably a peptidic or polypeptidic antagonist of the interaction between the Gp96 receptor and *E. coli* AIEC strains for the manufacture of a medicament for the prevention or treatment of inflammatory bowel disease or Crohn's disease. In particular such an antagonist is for use as an inhibitor of the interaction of the Gp96 receptor and *E. coli* AIEC strains, in particular its outer protein membrane OmpA. More particularly, this antagonist is for use as an inhibitor of the interaction of the Gp96 receptor and *E. coli* AIEC strains, in particular its outer protein membrane OmpA, in view of the prevention or treatment of an inflammatory bowel disease, such as ulcerative colitis (UC) and Crohn's disease (CD).

The invention therefore also relates to the use of an anti-Gp96 antibody for the manufacture of a medicament for the prevention or treatment of inflammatory bowel disease or Crohn's disease.

The invention therefore also relates to the use of an anti-OmpA antibody for the manufacture of a medicament for the prevention or treatment of inflammatory bowel disease or Crohn's disease.

Similarly to the use, the invention relates to a method for the prevention or treatment of an inflammatory bowel disease, such as ulcerative colitis (UC) and Crohn's disease (CD), wherein one administers, to a patient in need thereof, an efficient amount of an antagonist or pharmaceutical composition according to the invention. The various features presented above do apply to this subject-matter. Thus, the antagonist may be a Gp96 polypeptide, an OmpA polypeptide, an anti-Gp96 antibody, an anti-OmpA antibody, a siRNA, or a mixture thereof, as disclosed herein.

This method allows preventing and/or treating these disorders, based on the inhibition of the specific interaction between the intestinal epithelial cells and *E. coli* AIEC, and on the inhibition of potential invasion of these cells by this microorganism and/or other pathogens that may be present at the same time. This method may be applied to patients having Gp96 expression on the intestinal epithelial cells, in particular at the ileal level, especially at the apical plasma membrane of the ileal epithelial cells, and more specifically to such patients wherein *E. coli* AIEC is present or other pathogenic bacteria also expressing an outer membrane protein A able to recognize Gp96.

This method may comprise the administration to the same patient of a composition comprising an antagonist of the interaction between the CEACAM6 receptor and *E. coli* AIEC strains as disclosed above.

Another aspect of the present invention is an in vitro method for the diagnosis of inflammatory bowel disease, or of the determination of a predisposition of a person to develop inflammatory bowel disease, in which it is determined whether the level of expression of the Gp96 receptor in a biological sample from a subject to be tested is higher than the level of expression in a control sample, which is indicative of inflammatory bowel disease, or of a predisposition of the subject tested to develop inflammatory bowel disease.

In a preferred embodiment, the method is for the diagnosis of Crohn's disease.

In the context of the invention, a "biological sample" may be an ileal or colonic biopsy, a preparation of enterocytes isolated from an ileal or colonic biopsy, blood, buccal epithelial cells, or stool. The expression "ileal or colonic biopsy" is understood to mean a sample of part of the ileum or colon, or of the ileal or colonic mucosa, for example obtained during surgical resection or during endoscopy.

A "subject" or "patient" is a mammal, preferably a human being, regardless of sex, age and general condition. Children are also included. The test subject may be asymptomatic, or may be considered as being at risk of developing inflammatory bowel disease.

The term "diagnosis" refers to the determination or the confirmation of infection with inflammatory bowel disease, regardless of its stage of development. This may be more particularly an early diagnosis or a diagnosis of recidivation.

The method of the invention involves either the quantitative determination of the absolute level of expression of the Gp96 receptor, and then comparing with the level of expression of the receptor in a control subject, determined in parallel or otherwise known, or the direct determination of the relative level of expression of the Gp96 receptor in the biological sample to be tested compared with the control sample (the expression semi-quantitative detection may be used in this case). The "control" sample is a sample from a "healthy" subject or a subject not suffering from Crohn's disease, or a subject not suffering from any inflammatory bowel disease (IBD) or from colorectal cancer. This may, depending on the case, be a subject having inflammatory lesions of the small intestine of traumatic or infectious origin. In order to determine the progression of Crohn's disease, it may be useful to determine in a subject the level of expression of Gp96, and to control the effect of a medicament or the development of the disease, by testing the subject a second time, for example several weeks later. In this case, the results of the second test are compared with the results of the first test and in general also with the results obtained in a "healthy" subject. The "control" sample thus refers either to the same test subject or to the "healthy" subject.

The level of expression of the Gp96 receptor may be determined in various ways. It may be determined in particular by assaying the Gp96 receptor or by measuring its level of transcription, that is to say the quantity of mRNA which codes for the receptor. Various methods for the detection and/or quantification of the expression of the Gp96 receptor are described below.

According to a first embodiment, the level of expression of the Gp96 receptor is determined by measuring the quantity of Gp96 receptor glycoprotein, generally by bringing a biological sample into contact with a binding partner capable of selectively interacting with the Gp96 receptor present in the sample. The binding partner is generally an antibody, which may be polyclonal or monoclonal, preferably monoclonal. This may also be a peptide fragment of the Gp96 receptor. Antibodies may be obtained by the same manner than described above.

The quantity of Gp96 receptor glycoprotein is thus preferably measured by an immunological test comprising bringing the biological sample into contact with an optionally labelled anti-Gp96 antibody which specifically recognizes Gp96, and revealing the antibody-Gp96 receptor complexes formed.

According to a preferred embodiment, the biological sample is an ileal or colonic biopsy, and the immunological test is an immunohistochemical test.

The present invention also provides for a in vitro method for the diagnosis of inflammatory bowel disease, or of the determination of a predisposition of a person to develop inflammatory bowel disease, in which it is determined whether the level of expression of the Gp96 receptor and of the CEACAM 6 (Cd66c) (refer to WO2006/040481) in a biological sample from a subject to be tested is higher than the level of expression in a control sample, which is indicative of inflammatory bowel disease, or of a predisposition of the subject tested to develop inflammatory bowel disease.

The invention moreover provides an in vitro method for screening candidate substances for the prevention or treatment of inflammatory bowel disease, comprising:

(i) bringing the Gp96 receptor, in soluble form or expressed at the surface of the cell, into contact with at least one *E. coli* AIEC strain, in the presence or in the absence of a substance to be tested;

(ii) determining the capacity of the substance to specifically inhibit the interaction between the Gp96 receptor and said strain, and selecting and/or identifying said substance, In a preferred embodiment, the method is for screening candidate substances for the prevention or treatment of Crohn's disease.

Candidate substances may be of any type, including natural or synthetic compounds or mixtures of compounds. The substance may be structurally defined or of an unknown structure, for example in the form of a biological extract.

To determine the capacity of the candidate substance to inhibit the binding between the *E. coli* AIEC strains and the Gp96 receptor, standard competition tests may be performed on cell cultures expressing the Gp96 receptor. This may be, for example, cells genetically transformed in order to over-express the receptor, or enterocytes isolated from the ileal biopsy of patients suffering from Crohn's disease. They may be intestinal epithelial cells cultured in monolayers (by way of example HT29, Caco-2, T84, Intestine-407 cells). In the case where the candidate substance is an identified compound, it may be labelled, for example with a radioactive or non-radioactive marker (for example fluorescein).

The marker specifically bound to the Gp96 receptor may then be quantified in the presence of a variable concentration of said candidate substance, for example from $10^{-10}$ to $10^{-5}$ M. Alternatively, it is possible to monitor the competition between the candidate substance and the *E. coli* AIEC bacterium toward the Gp96 receptor by adhesion tests.

The following figures and examples illustrate the invention without limiting of the scope.

LEGEND OF THE FIGURES

FIG. 1. Gp96 expression in the intestinal biopsies of CD patients and controls. Quantification of Gp96 immunostaining using the SPOT BROWSER™ software, in TMA from colon and ileum biopsies of controls, patients in acute or quiescent phase of CD, **$P<0.01$.

Figure 2:
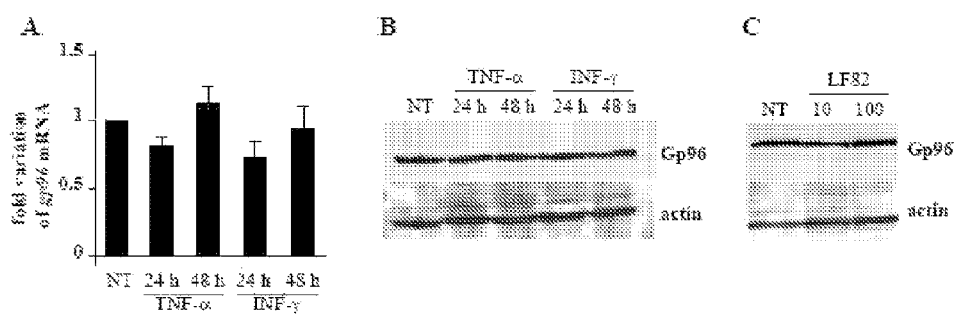

FIG. 2. Gp96 expression in Caco-2 cells. A. Fold variation of Gp96 mRNA levels in Caco-2 cells after 24 or 48 hours of stimulation with TNF-α or IFN-γ relative to that in non treated cells (NT) using RT-PCR. gapdh mRNA levels were measured as controls. Data are mean±SEM of three separate experiments. B-C. Western blot analysis showing expression levels of Gp96 by Caco-2 cells after 24 or 48 hours of stimulation with TNF-α or IFN-γ (B) or after a 3 hour infection period with AEC LF82 bacteria (C) at MOI 10 or 100. As loading control, a labelling was performed using anti-β-actin polyclonal antibodies.

Figure 3:
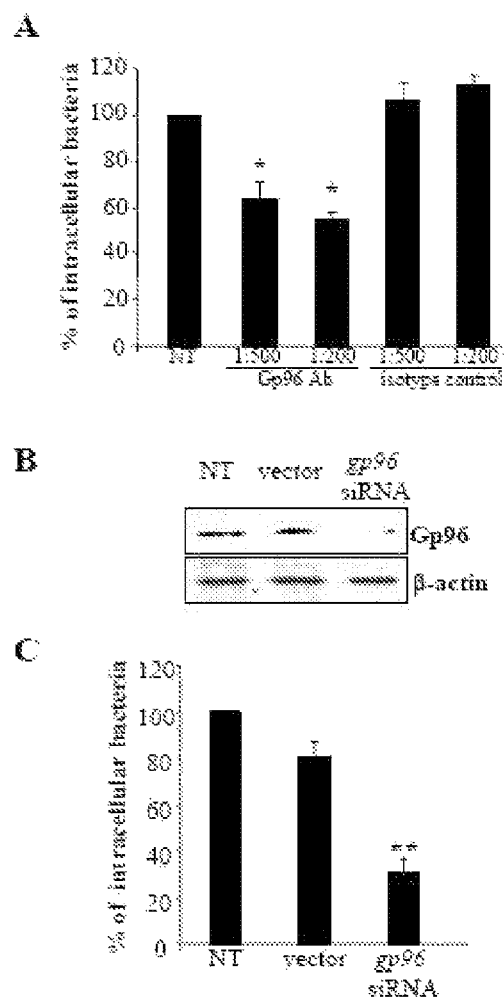

FIG. 3. Gp96 expression supports LF82 invasion. A. Effect of pretreatment of Intestine-407 epithelial cells with anti-Gp96 antibodies on the invasive level of LF82. Intestine-407 cells were pretreated with rabbit polyclonal antibodies raised against Gp96 (Gp96 Ab) or with rabbit polyclonal antibodies (isotype control) diluted 1:200 or 1:500 for 30 min and then infected by LF82 bacteria. Invasion was determined after a 3 h infection period and after gentamicin treatment for an additional hour. Results are expressed as intracellular bacteria relative to those obtained for strain LF82 on non treated cells (NT), taken as 100%. Each value is the mean±SEM of at least four separate experiments. *$P<0.05$ comparatively to the wild-type strain on untreated cells. B. Western blot analysis of whole protein extracts from Intestine-407 cells using anti-Gp96 and anti-β-actin antibodies. Intestine-407 cells were non transfected (NT), transfected with 10 ng of siRNA blocking Gp96 (Gp96 siRNA) or with empty vector (pSUPER) as control. C. Effect of gp96 siRNA on the invasive level of the wild-type strain LF82. Invasive bacteria were quantified as described in A. **$P<0.01$ compared to the wild-type strain on untreated cells.

FIG. 4. Gp96-dependent invasion involves AIEC OmpA. A. Invasion abilities with Intestine-407 epithelial cells of the LF82-.DELTA.ompA mutant, the LF82-.DELTA.ompA mutant transformed with the cloned LF82 ompA gene or the cloned K-12 MG1655 ompA gene or the pBAD33 vector alone. Invasive bacteria were quantified as described in FIG. 3A. **$P<0.01$ compared to the wild-type strain. Expression of type 1 pili was determined visually by yeast aggregation and the titre was recorded as the last dilution giving a positive aggregation results. Whole-cell lysates of LF82, LF82-.DELTA.ompA bacteria transformed with the cloned LF82 ompA gene, with the cloned K-12 ompA gene, or with the pBAD33 vector alone and grown in medium with L-arabinose, were separated by SDS-PAGE and stained with COOMASSIE BLUE™. The positions of OmpC/F and OmpA are marked. B. Effect of pretreatment of Intestine-407 epithelial cells with OMVs and anti-Gp96 antibodies (Gp96 Ab) on the invasive level of LF82-.DELTA.ompA. Intestine-407 cells were pretreated with rabbit polyclonal antibodies raised against Gp96 diluted 1:500 for 30 min, then pretreated with OMVs from WT or LF82-.DELTA.ompA bacteria for 1 h and after washing, cells were infected with bacteria. Invasive bacteria were quantified as described in FIG. 3A.

FIG. 5. Alignment of amino acids sequence of OmpA. Extracellular loop amino acids are in bold, and amino acids different between AIEC LF82 OmpA (SEQ ID NO: 2) and *E. coli* K-12 MG1655 (SEQ ID NO: 16) are underlined and in bold.

EXAMPLES

Materials and Methods

A. Patients and Biopsy Specimens

All patients included in this study were hospitalized in the Department of Gastroenterology (Archet II Hospital, University of Nice Sophia Antipolis, France) and provided a signed agreement for this study, and the protocol was approved by the local ethic committee of the University of Nice Sophia Antipolis. Intestinal biopsies were obtained from macroscopically inflamed mucosa of the terminal ileum and of the colon in 65 Crohn's disease (CD) patients (active CD) and from macroscopically non inflamed mucosa of the terminal ileum and of the colon in 55 CD patients (quiescent phase of the disease). There were 67 men and 53 women, with a mean age of 40 years (range 19-60) and mean disease duration of 10 years (range 2-23). Patients were all French Caucasians. In addition, biopsies were taken from the ileum and colon of 40 control patients consisting of individuals who had no significant pathological findings following endoscopic examination for changes in stool habits, abdominal pain, upper gastrointestinal bleeding or cancer surveillance.

B. Tissue Microarray (TMA) Construction and Immunohistochemistry

Representative intestinal biopsies obtained for each individual in building TMAs were selected from haematoxylin and eosin stained sections. Briefly, one tissue core (600 μm in diameter) was obtained from each specimen from the upper part of the mucosa, pits and glands were always cut longitudinally. The tissue cores were arrayed into a new paraffin block using a fine steel needle. The two final TMAs consisted of 480, 600 μm diameter tissue cores for ileum mucosa or colonic mucosa from patients and controls. Immunohistochemical methods were performed on serial 4 μm deparaffinized TMA sections processed as described by Hoffman et al. Monoclonal rat anti-Gp96 (9G10SPA-850, Stressgen) was used for 45 min at room temperature. After rinsing with PBS, sections were incubated with peroxidase-labeled anti-rat Igs (DAKO ENVISION™ System) for 45 min. For measurement of histological disease activity, the scoring system for histological abnormalities in CD mucosal biopsy specimens was used as used as used in Sandborn et al. [25]. After immunostaining, slides were analysed with an image analysis workstation (SPOT BROWSER™ version 7; Alphelys), as described by Hoffman et al. [24].

C. Bacterial Strains, Plasmids and Culture Conditions

Bacterial strains and plasmids used in this study are listed below. Bacteria were grown routinely in LB broth or on LB or Mueller-Hinton agar plates overnight at 37° C. Antibiotics were added at the following concentrations: ampicillin (50 μg/ml), kanamycin (50 μg/ml) and chloramphenicol (25 μg/ml). The LF82-ΔompA isogenic mutant was generated with a PCR product (Table 1), using the method described by Datsenko and Wanner [26] and modified by Chaveroche et al. [27]. For transcomplementation assays, a PCR product containing the entire ompA gene of AIEC LF82 or of E. coli K-12 MG1655 strain was cloned into the pBAD33 vector (Table 1).

Strains or plasmids:
LF82: E. coli: isolated from an ileal biopsy of a CD patient [6]
LF82-ΔompA: LF82 isogenic mutant with the ompA gene deleted
K-12 MG1655: non pathogenic E. coli strain (Laboratory stock)
pKOBEG: pBAD cloning vector harbouring λ phage redγβα operon, chloramphenicol$^r$ [27]
pBAD33: E. coli cloning vector, chloramphenicol$^r$ [29]
pPBI13: pBAD33 harbouring the 1.1 kb HindIII-SalI fragment with the entire ompA gene of strain LF82
pPBI14: pBAD33 harbouring the 1.1 kb HindIII-SalI fragment with the entire ompA gene of strain MG1655
pSUPER.neo: vector system for expression of short interfering RNA (Oligoengine)
gp96 siRNA: pSUPER.neo harbouring the oligonucleotide specific to the gp96 mRNA E. Cell Culture, Transfection and Invasion Assays Intestine-407 and Caco-2 cells were obtained from ATCC. A 19-mer oligonucleotide (5'UCAGUUGGAU GGA-UUAAAU 3' (SEQ ID NO: 16)specific to the gp96 mRNA) was selected for synthesis of siRNA, cloned into pSUPER vector (Oligoengine) and transfected with LIPO-FECTAMINE 2000 (Invitrogen INVITROGEN) according to the manufacturer's instructions. Bacterial invasion was quantified as described by Boudeau et al. [10]. Monolayers were infected for 3 h at a multiplicity of infection (MOI) of 10 bacteria per cell and the number of intracellular bacteria was determined as described by Boudeau [28]. Inhibition invasion assays were performed after a 30-min pretreatment of cells at 37° C. using anti-Gp96 (H-212, Santa Cruz Biotech) or rabbit IgG (isotype control, C-20, Santa Cruz Biotech). Pretreatment of IEC with OMVs was performed as previously described by Rolhion et al. [13]. For pretreatment of IEC with antibodies and OMVs, monolayers were incubated for 30 min with anti-Gp96 (diluted 1:500), next for 1 h with OMVs, then washed and infected.

F. mRNA Quantification

IEC were stimulated with 50 ng/ml of IFN-γ or TNF-α for 1 or 2 days. Total RNA were isolated using TRIZOL™ (INVITROGEN™) according to the manufacturer's instructions. cDNA were obtained using a 2-step reverse-transcriptase PCR kit (MP Biochemicals) and quantified using SYBR™ green TAG READYMIX™(sigma) with gp98 specific oligonucleotides (Table 1). Each sample was run in duplicate. All results were normalized to the unaffected housekeeping gapdh gene.

TABLE 1

Oligonucleotides used for PCR experiments

| Primer | SEQ ID NO: | Oligonucleotide sequence (5'-3') | PCR product size (bp) | use |
|---|---|---|---|---|
| A2GBL-3 | 4 | AAAGCCACGTTGTGTCTCAA | 957 | kanamycin resistance cassette amplification |
| B2GBLnp5 | 5 | TTAGAAAAACTCATCGAGCA | | |
| MIompA(R) | 6 | AAAGGCAAAAAAAACCCCGCAGCGGGG TTTTTCTACCAGACGAGAACTTAGAAAAA CTCATCGAGCA | 1097 | ΔompA isogenic mutant construction |
| MIompA(F) | 7 | CTCGTTGGAGATATTCATGGCGTATTTTG GATGATAACGAGGCGCAAAAAAAAGCCA CGTTGTGTCTCAA | | |
| OmpA1 | 8 | GGAGCCGGAGCAACTACTGG | 205 | isogenic mutant verification |
| OmpA2 | 9 | ACGACACCGGCGTTTCTCCG | | |
| OmpA3 | 10 | GCAGGCATTGCTGGGTAAGG | 1232 | isogenic mutant verification and sequencing |
| OmpA4 | 11 | AATATTGAGCAGATCCCCCGG | | |
| OmpASalI | 12 | ACGCGTCGACCGTTGGAGATATTCATGG CG | 1098 | cloning of ompA gene |
| OmpAHindIII | 13 | CCCAAGCTTGGGAGACGAGAACTTAAGC CTGC | | |
| Gp96-upstream | 14 | GGGTGTGGTGGACTCAGATG | 669 | Gp96 quantification by q-RT PCR (Schreiter et al) |
| Gp96-downstream | 15 | GTTGCCAGACCATCCGTACT | | |

D. OMV Preparation

OMVs were isolated as described by Rolhion et al. [13]. The culture supernatants were filtered and OMVs collected by ultra-centrifugation at 150,000×g for 3 h at 4° C. OMV pellets were resuspended in 10 mM Tris-HCl pH 8.0, 150 mM NaCl.

G. Yeast Cell Aggregation Assays

Yeast cell aggregation assays were performed as described by Rolhion et al. [13].

H. Protein Preparation and Analysis

Bacteria, grown with L-arabinose, were resuspended in SDS-PAGE loading buffer and equivalent amounts of protein extract were separated by SDS-12% PAGE and stained by COOMASSIE™. IEC, stimulated with IFN-γ, or TNF-α, or infected by bacteria at MOI 10 or 100, were lysed as described by Barnich et al. [12]. 10 μg of proteins were separated by SDS-12% PAGE, blotted onto nitrocellulose membranes (Amersham International), and stained using rat anti-Grp94 monoclonal antibody (9G10, SPA-850, Stressgen) for Gp96 and goat anti-human β-actin polyclonal antibody (C-11, Santa Cruz Biotech) for β-actin.

I. Statistical Analysis

For analysis of the significance of difference in Gp96 immunostaining, assays were compared using the Student's t-test. Values are expressed as the mean±SEM of 'n' number of experiments. The association of Gp96 expression with categorical pathological features was made using X2 analysis. Calculations and analyses were performed with SPSS 11.5 for Windows, and where appropriate, were two-tailed. Student's t-test was used for analysis of the statistical significance between invasion levels. P-values less than or equal to 0.05 were considered statistically significant.

Example 1

Increase of Gp96 Protein Expression in the Ileal Intestinal Epithelium of CD Patients Quantification of Gp96 immunostaining shows that positive cell densities in ileal biopsies of patients with acute or quiescent phase of CD is significantly higher than those observed in controls (FIG. 1). Conversely, very few positive cells are observed in colon biopsies from controls and CD subjects. In CD patients with active phase, Gp96-immunostaining was observed in 33/65 (50%) individuals, whereas in CD patients with quiescent phase, Gp96 immunostaining was observed in 19/55 (34%) individuals.

Example 2

Influence of Inflammatory Conditions or AIEC Infection on Gp96 Expression

To investigate whether abnormal Gp96 expression in CD patients results from stimulation by pro-inflammatory cytokines or *E. coli* infection of ileal epithelial cells, Gp96 expression is analysed in cultured IEC after stimulation with IFN-γ or TNF-α or after infection with AIEC bacteria. No modification in gp96 mRNA levels is observed in Caco-2 cells after TNF-α or IFN-γ stimulation for 24 or 48 hours compared to non-treated cells (FIG. 2A). In addition, Western-blot analysis using anti-Gp96 antibodies indicates a similar Gp96 expression in pro-inflammatory cytokine stimulated or unstimulated Caco-2 cells (FIG. 2B). The Gp96 protein level is not modified in Caco-2 cells after 3 hours of infection by AIEC strain LF82 at a MOI of 10 or 100 (FIG. 2C). Similar results are observed with Intestine-407 cells. Thus, inflammatory conditions or AIEC infection do not modify Gp96 expression in IEC.

Example 3

Influence of Gp96 Expression on LF82 *E. coli* Invasion

The role of Gp96 in AIEC invasion of IEC is investigated using invasion inhibition assays in the presence of anti-Gp96 polyclonal antibodies and by invasion assays using IEC with decreased levels of gp96 by RNA silencing. When the IEC are pretreated with anti-Gp96 antibodies (dilution 1:200), the invasion level of LF82 bacteria is 54.5%±3.3% of that of strain LF82 on untreated cells (FIG. 3A). In contrast, pretreatment with anti-IgG isotype control has no effect on LF82 invasion. Interestingly, reduced Gp96 expression by transfecting IEC with gp96 siRNA (FIG. 3B) induces a decreased LF82 invasion levels (FIG. 3C). Indeed, the invasion levels of LF82 bacteria on Intestine-407 cells transfected with Gp96 siRNA are 30.9%±5.0% of that of strain LF82 on untreated cells. In contrast, transfection of cells with an empty vector that did not reduce Gp96 protein level, does not affect the ability of AIEC LF82 to invade IEC. Taken together, these results strongly suggest that Gp96 plays a major role in AIEC invasion.

Example 4

Influence of OmpA on LF82 *E. coli* Invasion (FIG. 4A)

The role of OmpA in AIEC strain LF82 is investigated. LF82 isogenic mutant with the ompA gene deleted was constructed and we observe that the LF82-ΔompA presents no defect in type 1 pili expression. Electronic microscopic examination of negatively stained bacteria indicates that the bacteria expressed type 1 pili and similar titres (1/8) of yeast cell aggregation are obtained compare to the wild-type strain LF82, indicating that the LF82-ΔΔmpA isogenic mutant synthesizes similar levels of functional type 1 pili to the wild-type strain LF82. Quantitative invasion assay shows that the LF82-ΔompA mutant has a reduced ability to invade intestine-407 epithelial cells, with a 56.3%±2.6% residual invasion level compared to wild-type strain LF82, taken as 100% (FIG. 4A). Transcomplementation with the cloned ompA gene of AIEC LF82 fully restores the invasion of the mutant. Analysis of OmpA sequences reveals that the LF82 OmpA differed from that of non pathogenic *E. coli* K-12 strain MG1655 by five amino acids: two amino acids located in one of the periplasmic domain, one in the transmembrane domain and two in the third extracellular loop of the OmpA protein (FIG. 5). Transformation of LF82-ΔompA mutant with cloned ompA gene of *E. coli* K-12 strain MG1655 does not restore invasion to a level similar to that of the wild-type LF82. This is not due to defects in OmpA expression since the amounts of OmpA produced are similar in LF82-ΔompA bacteria transcomplemented with cloned ompA from AIEC LF82 or cloned ompA from *E. coli* K-12.

Example 5

Ability of LF82 OMVs to Restore the Invasion of LF82-ΔompA (FIG. 4B)

The ability of LF82 OMVs to restore the invasion of LF82-ΔompA isogenic mutant is analyzed. The invasion level of the LF82-ΔompA mutant is increased when the IEC were pretreated with LF82 OMVs, reaching 85.2%±5.3%, and is not significantly different from that of strain LF82 taken as 100%. On the host side, this involved Gp96 as addition of anti-Gp96 polyclonal antibodies blocks the restoration of the invasion level of the LF82-ΔompA mutant with LF82 OMVs-treated cells. On the bacterial side, this involved OmpA, as no increase in the invasion level of the LF82-ΔompA mutant is observed with IEC pretreated with LF82-ΔompA OMVs.

Heat Shock Protein 90 kDa Beta (Grp94 ou Gp96), Member 1 [*Homo sapiens*]

SEQ ID NO: 1

```
  1 mralwvlglc cvlltfgsvr addevdvdgt veedlgksre gsrtddevvq reeeaiqldg
 61 lnasqirelr eksekfafqa evnrmmklii nslyknkeif lrelisnasd aldkirlisl
121 tdenalsgne eltvkikcdk eknllhvtdt gvgmtreelv knlgtiaksg tseflnkmte
181 aqedgqstse ligqfgvgfy saflvadkvi vtskhnndtq hiwesdsnef sviadprgnt
241 lgrgttitlv lkeeasdyle ldtiknlvkk ysqfinfpiy vwssktetve epmeeeeaak
301 eekeesddea aveeeeekk pktkkvektv wdwelmndik piwqrpskev eedeykafyk
361 sfskesddpm ayihftaege vtfksilfvp tsaprglfde ygskksdyik lyvrrvfitd
421 dfhdmmpkyl nfvkgvvdsd dlplnvsret lqqhkllkvi rkklvrktld mikkiaddky
481 ndtfwkefgt niklgviedh snrtrlakll rfqsshhptd itsldqyver mkekqdkiyf
541 magssrkeae sspfverllk kgyeviylte pvdeyciqal pefdgkrfqn vakegvkfde
601 sektkesrea vekefeplln wmkdkalkdk iekavvsqrl tespcalvas qygwsgnmer
661 imkaqayqtg kdistnyyas qkktfeinpr hplirdmlrr ikededdktv ldlavvlfet
721 atlrsgyllp dtkaygdrie rmlrlslnid pdakveeepe eepeetaedt tedteqdede
781 emdvgtdeee etakestaek del
```

OmpA Strain LF82

SEQ ID NO: 2

```
MKKTAIAIAVALAGFATVAQAAPKDNTWYTGAKLGWSQYHDTGFFTINN
NGPTHENQLGAGAFGGYQVNPYVGFEMGYDWLGRMPYKGSVENGAYKAQ
GVQLTAFTKLGYPITDDLDVYTRLGGMVWRADTKSNPDGKNHDTGVSPV
FAGGVEYAITPEIATRLFTEYQWTNNIGDAHTIGTRPDNGMLSLGVSYR
FGQGEAAPVVAPAPAPAPEVQTKHFTLKFTSDVLFTFNKATLKPEGQAA
LDQLYSQLSNLDPKDGSVVVLGYTDRIGSDAYNQALSERFTRAQSVVDY
LISKGIPADKISARGMGESNPVTGNTCDNVKQRAALIDCLAPDRRVEIE
VFTKGIKDVVTQPQA
```

BIBLIOGRAPHIC REFERENCES

1—Strober W, Fuss I, Mannon P, J Clin Invest 2007; 117:514-21.
2—Xavier R J, Podoisky D K, Nature 2007; 448:427-34.
3—Sartor R B, Gastroenterology 2008; 134:577-94.
4—Baumgart M et al., ISME J 2007; 1:403-18.
5—Conte M P et al., Gut 2006; 55:1760-7.
6—Darfeuille-Michaud A et al., Gastroenterology 1998; 115:1405-13.
7—Kotlowski R et al., Gut 2007; 56:669-75.
8—Martin H M et al., Gastroenterology 2004; 127:80-93.
9—Sasaki M et al., Lab Invest 2007; 87:1042-54.
10—Boudeau J et al., Infect Immun 1999; 67:4499-509.
11—Darfeuille-Michaud A et al., Gastroenterology 2004; 127:412-21.
13—Rolhion N et al., J Bacteriol 2005; 187:2286-96.
14—Kuehn M J, Kesty N C, Genes Dev 2005; 19:2645-55.
15—Mashburn-Warren L M et al., Mol Microbiol 2006; 61:839-46.
16—Nicholson T F et al., Infect Immun 2009.
17—Torres A G, Kaper J B, Infect Immun 2003; 71:4985-95.
18—Weiser J N, Gotschlich E C, Infect Immun 1991; 59:2252-8.
19—Prasadarao N V, Infect Immun 2002; 70:4556-63.
20—Prasadarao N V et al., Infect Immun 2003; 71:1680-8.
21—Cabanas D et al., EMBO J 2005; 24:2827-38.
22—Heazlewood C K et al., PLoS Med 2008; 5:e54.
23—Kaser A et al., Cell 2008; 134:743-56.
24—Hofman P et al., Br J Cancer 2008; 98:956-64.
25—Sandborn W J et al., Gastroenterology 2002; 122:512-30.
26—Datsenko K A, Wanner B L. Proc Natl Acad Sci USA 2000; 97:6640-5.
27—Chaveroche M K et al., Ghigo J M, d'Enfert C. Nucleic Acids Res 2000; 28:E97.
28—Boudeau J et al., Barnich N, Darfeuille-Michaud A. Mol Microbiol 2001; 39:1272-84.
29—Guzman L M et al., J Bacteriol 1995; 177:4121-30.
30—Yang et al., 2007, Immunity, 26, 215-226
31—Rolhion et al., 2010, Gut, 59: 1355-1362.

The invention claimed is:

1. A method of inhibiting the specific interaction between the outer membrane protein A (OmpA) of an adherent-invasive *E. coli* and the Gp96 endoplasmic reticulum localized stress response chaperone polypeptide expressed on ileal epithelial cells in patients having Crohn's disease or at risk of developing Crohn's disease, comprising administering to a patient having the Gp96 endoplasmic reticulum localized stress response chaperone polypeptide expressed on ileal epithelial cells, an anti-Gp96 antibody with a pharmaceutically acceptable carrier in an amount effective to inhibit the specific interaction between the Gp96 endoplasmic reticulum localized stress response chaperone polypeptide expressed on the ileal epithelial cells and the OmpA of the adherent-invasive *E. coli*.

2. A method of inhibiting the specific interaction between the outer membrane protein A (OmpA) of an adherent-invasive *E. coli* and the Gp96 endoplasmic reticulum localized stress response chaperone polypeptide expressed on ileal epithelial cells in patients having Crohn's disease or at risk of developing Crohn's disease, and invasion of the ileal epithelial cells by the adherent-invasive *E. coli* in the patients, comprising administering to a patient having the Gp96 endoplasmic reticulum localized stress response chaperone polypeptide expressed on ileal epithelial cells, an anti-Gp96 antibody with a pharmaceutical acceptable carrier in an amount effective to inhibit the specific interaction between the Gp96 endoplasmic reticulum localized stress response chaperone polypeptide expressed on the ileal epithelial cells and the OmpA of the adherent-invasive *E. coli* and the invasion of the ileal epithelial cells by the adherent-invasive *E. coli*.

3. The method of claim 1, wherein the anti-Gp96 antibody binds specifically to the Gp96 endoplasmic reticulum localized stress response chaperone polypeptide of SEQ ID NO: 1.

4. The method of claim 2, wherein the anti-Gp96 antibody binds specifically to the Gp96 endoplasmic reticulum localized stress response chaperone polypeptide of SEQ ID NO: 1.

\* \* \* \* \*